(12) United States Patent
Mirzaee

(10) Patent No.: US 6,585,926 B1
(45) Date of Patent: Jul. 1, 2003

(54) METHOD OF MANUFACTURING A POROUS BALLOON

(75) Inventor: Daryush Mirzaee, Sunnyvale, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 166 days.

(21) Appl. No.: 09/653,273

(22) Filed: Aug. 31, 2000

(51) Int. Cl.⁷ .............................................. B23K 26/00
(52) U.S. Cl. ...................... 264/400; 264/156; 264/291; 264/473; 264/482; 264/485; 264/DIG. 73; 219/121.7; 219/121.71; 604/96.01; 604/104
(58) Field of Search .................. 264/400, 482, 264/155, 156, 504, 516, 291, 473, 485, DIG. 73; 219/121.7, 121.71; 604/96.01, 104

(56) References Cited

U.S. PATENT DOCUMENTS

| | | | |
|---|---|---|---|
| 5,049,132 A | 9/1991 | Shaffer et al. | 604/101 |
| 5,087,394 A * | 2/1992 | Keith | 204/22 |
| 5,213,576 A | 5/1993 | Abiuso et al. | 604/96 |
| 5,254,089 A | 10/1993 | Wang | 604/96 |
| 5,306,250 A * | 4/1994 | March et al. | 604/104 |
| 5,318,531 A | 6/1994 | Leone | 604/96 |
| 5,405,472 A | 4/1995 | Leone | 156/218 |
| 5,411,477 A * | 5/1995 | Saab | 604/96 |
| 5,456,661 A * | 10/1995 | Narciso, Jr. | 604/20 |
| 5,620,420 A | 4/1997 | Kriesel | 604/133 |
| 5,707,385 A * | 1/1998 | Williams | 606/192 |
| 5,728,068 A | 3/1998 | Leone et al. | 604/101 |
| 5,800,392 A | 9/1998 | Racchini | 604/96 |
| 5,823,996 A | 10/1998 | Sparks | 604/96 |
| 5,833,659 A | 11/1998 | Kranys | 604/96 |
| 5,843,033 A | 12/1998 | Ropiak | 604/96 |
| 5,860,954 A | 1/1999 | Ropiak | 604/96 |
| 5,876,426 A * | 3/1999 | Kume et al. | 607/88 |
| 5,921,416 A * | 7/1999 | Uchara | 215/12.1 |
| 6,045,899 A | 4/2000 | Wang et al. | 428/315.7 |
| 6,090,330 A * | 7/2000 | Gawa et al. | 264/400 |

* cited by examiner

*Primary Examiner*—Stefan Staicovici
(74) *Attorney, Agent, or Firm*—Squire, Sanders & Dempsey, L.L.P.

(57) ABSTRACT

A method of manufacturing a porous elastic membrane that may be used in a balloon assembly of a balloon catheter is described. In the method, an elastic membrane material is expanded beyond an intended deployment expansion to a hyper-expanded state. Apertures are then formed in the hyper-expanded material. After contraction, the now-porous membrane can be used to form the outer wall of the balloon assembly. An aperture formed in the hyper-expanded membrane will have a smaller diameter than when the balloon is inflated to a smaller deployment expansion in the patient's body.

16 Claims, 4 Drawing Sheets

METHOD OF MANUFACTURING A POROUS BALLOON

BACKGROUND

1. Field of the Invention

This invention relates to a method of manufacturing a porous elastic membrane, and in particular a porous membrane that can be used to form the walls of a balloon assembly of a balloon catheter.

2. Description of Related Art

During a medical procedure known as percutaneous transluminal coronary angioplasty ("PTCA"), a balloon catheter is inserted into an artery. A balloon assembly of the balloon catheter is then inflated to compress an atherosclerosis and dilate the walls of the artery. A therapeutic agent is then administered to the inner walls of the artery through small apertures in the outside wall of the balloon assembly. The balloon catheter's capability to locally administer a therapeutic agent to the dilated portion of the artery can be effective in limiting restenosis.

Porous, elastic balloons and methods of making such balloons are disclosed in U.S. Pat. No. 5,318,531 to Leone; U.S. Pat. No. 5,049,132 to Shaffer et al.; U.S. Pat. No. 5,860,954 to Ropiak; and U.S. Pat. No. 5,254,089 to Wang. The apertures through the balloon may be formed by mechanical punching, mechanical drilling, directing a laser beam at the elastic material, directing an ion beam at the elastic material, or directing an electron beam at the elastic material, among other possibilities. Typically, the cost of making the apertures is inversely proportional to their diameters.

Apertures formed by mechanical drilling or poking are not always of the precise shape and size desired, or may have tiny flaws which could affect the smooth delivery of therapeutic agents. Moreover, the size of the aperture is limited by the ability to make ever finer tools. Apertures formed using a laser, an ion beam, or an electron beam, while potentially having smaller and more regular diameters, are time consuming and expensive to make. Accordingly, there is a need for an inexpensive method of precisely forming tiny apertures in an elastic membrane for use in a balloon catheter.

SUMMARY

The present invention provides methods for forming a porous membrane, which may be used, for example, to form the outside wall of a balloon assembly of a balloon catheter.

One embodiment of the present invention includes expanding an elastic material beyond an intended deployment expansion to a hyper-expanded expansion. A plurality of apertures are formed through the hyper-expanded elastic material. The diameter of the apertures as formed is larger than the diameter of the apertures at the intended deployment expansion.

In accordance with another embodiment of the present invention, a method for forming a porous balloon is provided. The method includes forming a balloon of an elastic material. The balloon has an outer wall with an intended deployment diameter D1. The balloon is inflated to a diameter D2, wherein D2 is greater than D1. A plurality of apertures are formed in the outer wall. The apertures so formed have a diameter d2. The balloon is then deflated for insertion into a patient's body. In the patient's body, the balloon is inflated to the intended deployment diameter D1, at which point the apertures have an intended deployment diameter of $d_1$. Diameter $d_1$ is less than the diameter $d_2$ of the apertures when the apertures were formed.

Since the cost and time required to make a porous membrane for a balloon catheter or some other device is a function of the aperture size, with smaller holes being more costly and time consuming to make, the present invention provides for significant savings.

DETAILED DESCRIPTION

Figure 1A:
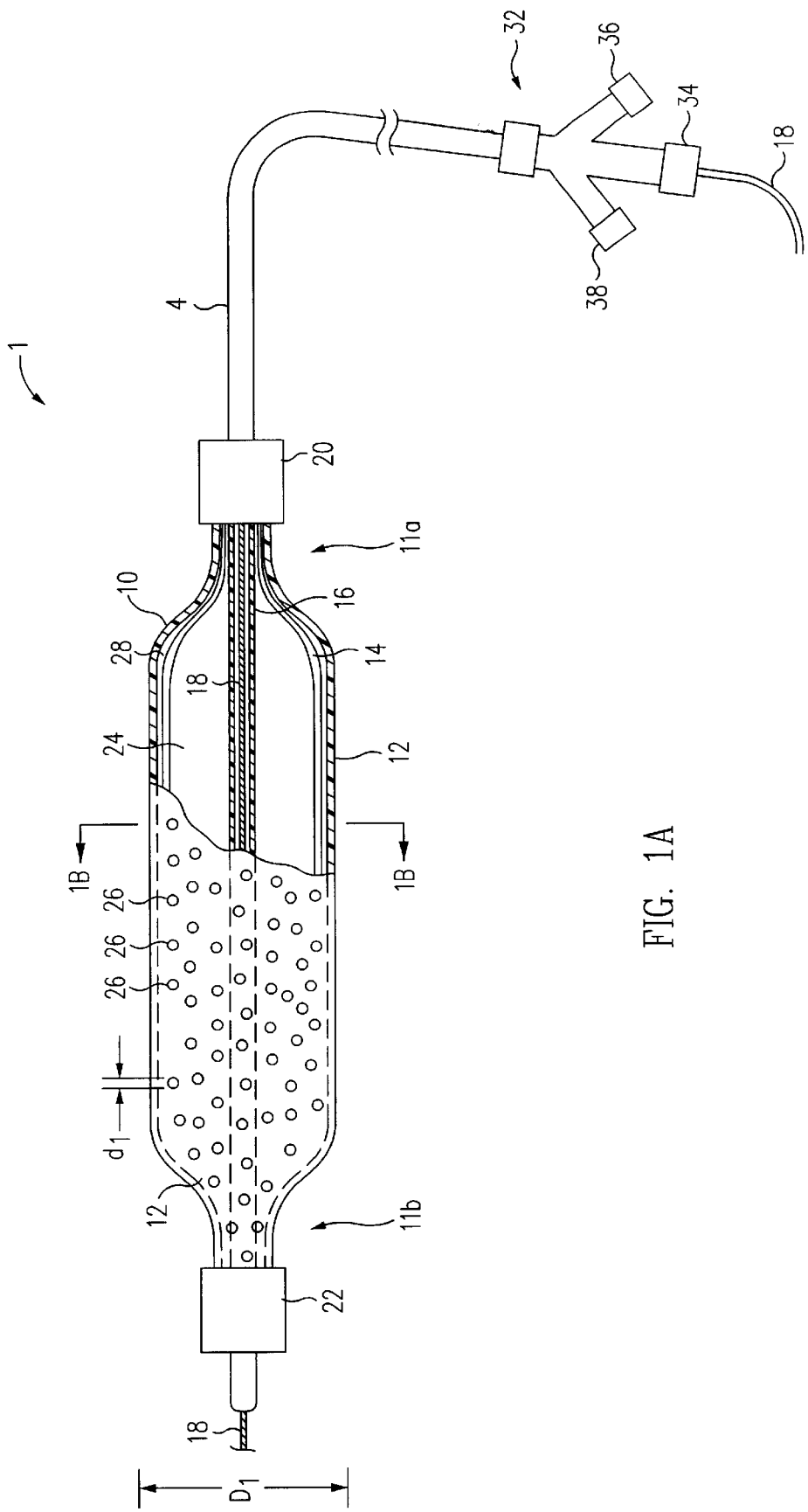
FIG. 1A shows a balloon assembly having a balloon assembly with a porous outer wall.
Figure 1B:
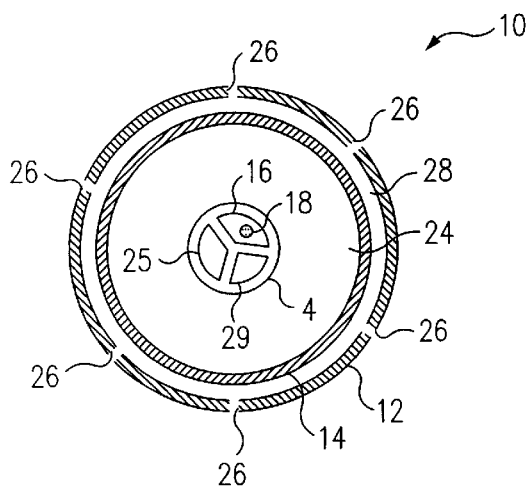
FIGS. 1B, 1C, and 1D show cross-sections of balloon catheter assemblies in accordance with various embodiments of the present invention.

FIG. 1A is a partial view of an exemplary balloon catheter 1 that may be used in a variety of medical procedures, such as percutaneous transluminal coronary angioplasty ("PCTA") and vascular prosthetic implantation, among other possibilities. FIG. 1B is a cross-sectional view of catheter assembly 1 of FIG. 1A taken along the line 1B—1B.

Balloon catheter 1 includes a catheter tube 4 having a guidewire lumen 16. Guidewire lumen 16 is configured to receive a guidewire 18 that is used to maneuver catheter tube 4 through an anatomical passageway of a patient. Balloon catheter 1 may be used in various body areas, such as blood vessels, urinary tract, intestinal tract, kidney ducts, wind pipes, and the like.

A balloon assembly 10 is provided at a distal end of catheter tube 4. Balloon assembly 10 has a pair of opposing ends 11a, 11b, which are engaged to catheter tube 4 at proximal collar 20 and distal collar 22, respectively, to define a balloon chamber. Balloon assembly 10 includes an outer wall 12 and an inner wall 14. Balloon assembly 10 is selectively inflatable to dilate from a collapsed configuration to a desired and controlled expanded configuration.

Outer wall 12 and inner wall 14 can have any suitable thickness so long as the thickness does not compromise properties that are important for achieving optimum performance. Such properties include high burst strength, good flexibility, high resistance to fatigue, an ability to fold, an ability to cross and re-cross a desired region of treatment or an occluded region in a body lumen, and a low susceptibility to defects caused by handling, among other possibilities.

Balloon assembly 10 can be selectively inflated by supplying a fluid into interior inflation port 36, through interior inflation lumen 25, and into an interior region 24 of balloon assembly 10. Interior region 24 is within inner wall 14. The pressure supplied by the fluid into interior region 24 may range, for example, from 1 to 25 atmospheres. Balloon assembly 10 is selectively deflatable after inflation to return to a collapsed configuration or a deflated profile to facilitate the removal of catheter assembly 1 from the patient's body.

In FIGS. 1A and 1B, balloon assembly 10 is shown expanded to its intended deployment configuration. The intended deployment configuration is achieved by supplying fluid into interior region 24 to inflate balloon assembly 10 until the outer diameter of balloon assembly 10 reaches an intended deployment balloon diameter $D_1$. This intended deployment balloon diameter $D_1$ is typically defined by the diameter of the body passage, such as a coronary artery, in which balloon assembly 10 is to be used. When balloon assembly 10 is inflated to its intended deployment balloon diameter $D_1$, the material forming outer wall 12 is expanded to its intended deployment expansion. Exemplary deployment diameters may range from 1.5 to 5.0 mm at internal pressures of up to 25 atmospheres. These parameters, like the other numerical values provided herein, are exemplary and not limiting.

A plurality of small apertures 26 are present in the outer wall 12 of balloon assembly 10. The number of apertures 26 and the diameter of apertures 26 can be varied, depending on the desired application. The deployment diameter $d_1$ of apertures 26 is the diameter of apertures 26 when balloon assembly 10 is expanded to its intended deployment diameter $D_1$. The deployment diameters $d_1$ of apertures 26 are not shown to scale in FIGS. 1A and 1B (or in the other figures), and may range, for example, from 0.5 to 10 μm in diameter.

Therapeutic agents may be provided through apertures 26 in outer wall 12 and into the surrounding artery or other passageway or cavity. The expression "therapeutic agent", as used herein, broadly refers to an agent or substance that possesses desirable therapeutic, diagnostic, or other medicinal or bioactive characteristics. The therapeutic agent may be, for example, antineoplastic, antimitotic, antiinflammatory, antiplatelet, anticoagulant, antifibrin, antithrombin, antiproliferatve, antibiotic, antioxidant, and antiallergic substances, as well as combinations thereof.

Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany) methotrexate, azathioprine, vincristine, vinblastine, fluorouracil, doxorubicin hydrochloride (e.g., Adriamycin® from Pharmacia & Upjohn, Peapack, N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone.

While the preventative and treatment properties of the exemplary therapeutic agents listed herein are well-known to those of ordinary skill in the art, these therapeutic agents are provided by way of example and are not meant to be limiting. Other therapeutic agents are equally applicable for use with the disclosed embodiments.

In one embodiment, interior region 24 of balloon assembly 10 of FIGS. 1A and 1B is filled with a first fluid from interior inflation lumen 25 for expansion purposes. The first fluid is contained within inner wall 14. After the expansion of balloon assembly 10 to deployment size, a second fluid containing the desired therapeutic agent is administered into delivery port 38, through delivery lumen 29, and into a concentric interior region 28 that is between inner wall 14 and outer wall 12. From concentric interior region 28, the therapeutic agent can flow out of apertures 26 in outer wall 12 and into the patient's body.

Figure 1C:
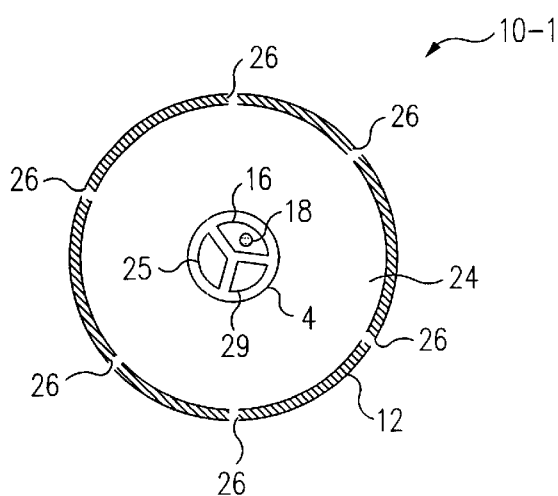

In an alternative embodiment shown in FIG. 1C, balloon assembly 10-1 does not include an inner wall 14. In this embodiment, the therapeutic agent (with or without carrier fluids) is provided into interior region 24, thereby creating an internal pressure and expanding outer wall 12 of balloon assembly 10-1 to deployment diameter $D_1$. The therapeutic agent then passes out of apertures 26 and into the patient's body.

Figure 1D:
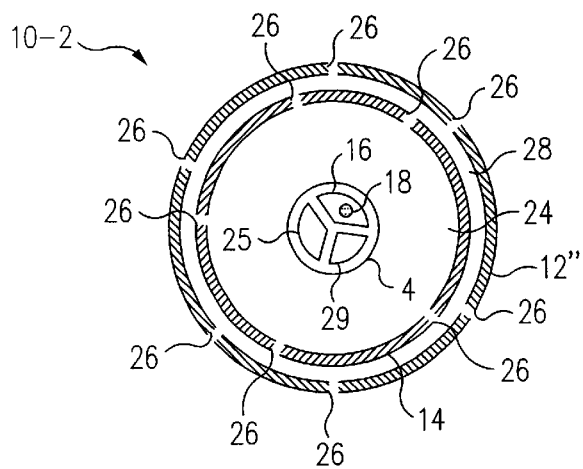

In yet another embodiment shown in FIG. 1D, apertures 26 also are present through inner wall 14 of balloon assembly 10-2. The apertures in inner wall 14 enable the therapeutic agent to be pushed slowly at low pressure out of inner wall 14 into interior region 28, and then out of apertures 26 of outer wall 12 into the patient's body.

Various materials can be subjected to the aperture-forming methods described herein for use in balloon assemblies like those shown in FIGS. 1A, 1B, 1C, and 1D. For example, polyethylene terephthalate (PET), polyurethane, latex, or silicone may be used.

The methods described herein also can be used to make balloon assemblies that employ a plurality of elastic materials. For example, balloon assembly 10-2 of FIG. 1D may have an inner wall 12 formed of porous PET, and an outer wall 12 formed of porous polyurethane, latex, or silicone, which typically are more elastic than PET.

Figure 2:
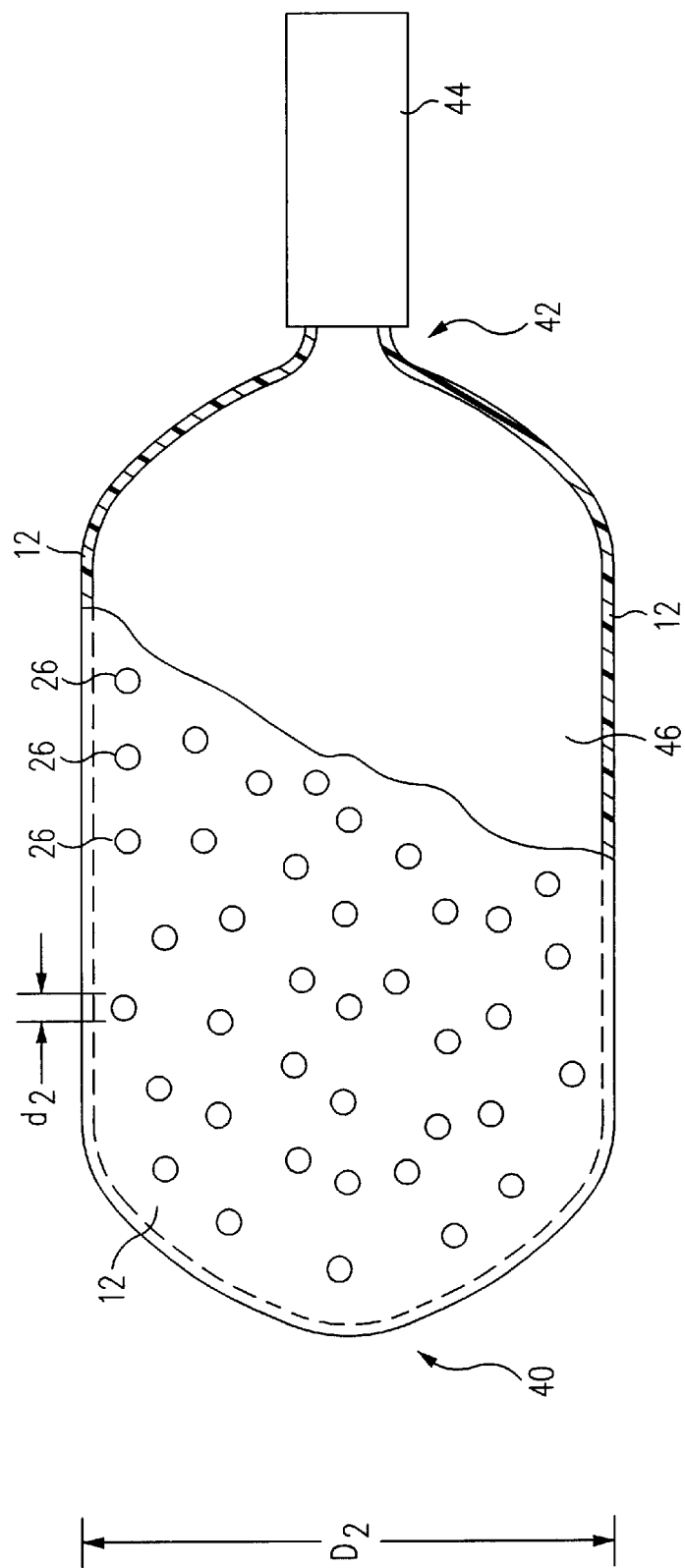
FIG. 2 shows a membrane of a balloon catheter in a hyper-expanded state.

In accordance with one embodiments of the present invention, apertures 26 may be formed by inflating outer wall 12 to a hyper-expanded diameter $D_2$, as shown in FIG. 2. The hyper-expanded diameter $D_2$ is larger than the intended deployment diameter $D_1$ shown in FIG. 1. For example, hyper-expanded diameter $D_2$ may be 25 to 50 percent greater, or two or three times larger than deployment diameter $D_1$. The amount of hyper-expansion may vary depending on the materials used, the tools available for making apertures 26, and the intended deployment diameter of $d_1$, among other possibilities.

The expansion of outer wall 12 to a hyper-expanded state can be performed using various techniques. For example, in one embodiment, outer wall 12 (or inner wall 14 of FIG. 1D) is formed using blow-molding into a closed cylindrically-shaped membrane having an interior region 46. Referring to FIG. 2, first end 40 of the cylindrically-shaped membrane is closed and an opposite end 42 is attached to a pressure source 44. Pressure source 44 fills interior region 46 with a pressurized gas or other fluid, which inflates outer wall 12 to the desired hyper-expanded diameter $D_2$. Subsequently, apertures 26 are formed in the hyper-expanded outer wall 12 using any of a number of aperture-forming processes. For example, apertures 26 may be formed using laser, track etch, or mechanical drilling processes, among other possibilities. In an embodiment in which, as apertures 26 are being formed, the gas or other fluid passes through the apertures, pressure source 44 maintains the pressure in interior region 46 by, for example, maintaining a continuous flow of the gas or other fluid into interior region 46. After the formation of apertures 26, outer wall 12 is removed from pressure source 44 and the sealed portion of first end 40 is cut off. Outer wall 12 can be mounted onto catheter tube 4 to form balloon assembly 10. For a two-wall balloon, such as in FIG. 1D, the inner and outer walls are typically formed and punctured in separate steps before they are mounted on the balloon assembly.

Apertures 26 that are formed to have a diameter $d_2$ while balloon assembly 10 is in its hyper-expanded state $D_2$ will have a proportionally smaller diameter $d_1$ (see FIG. 1A) when balloon assembly 10 is inflated in the patient's body to its intended deployment diameter $D_1$. Since, as a general matter, the time and cost to manufacture a porous membrane increases as the diameter of apertures 26 decreases, the present invention can provide savings in both manufacturing time and cost.

For example, assume that balloon catheter 10 of FIG. 1A is hyper-expanded to a diameter $D_2$ that is two times the deployment diameter, $D_1$. A mechanical drilling technique that would conventionally form apertures 26 having a diameter of 8 to 10 $\mu$m would result in an aperture 26 having a deployment diameter $d_1$ of 4 to 5 $\mu$m. Similarly, a laser process that would conventionally form an aperture 26 having a diameter of 7 to 8 $\mu$m would result in an aperture 26 having a deployment diameter $d_1$ of 3.5 to 4 $\mu$m.

Figure 3:
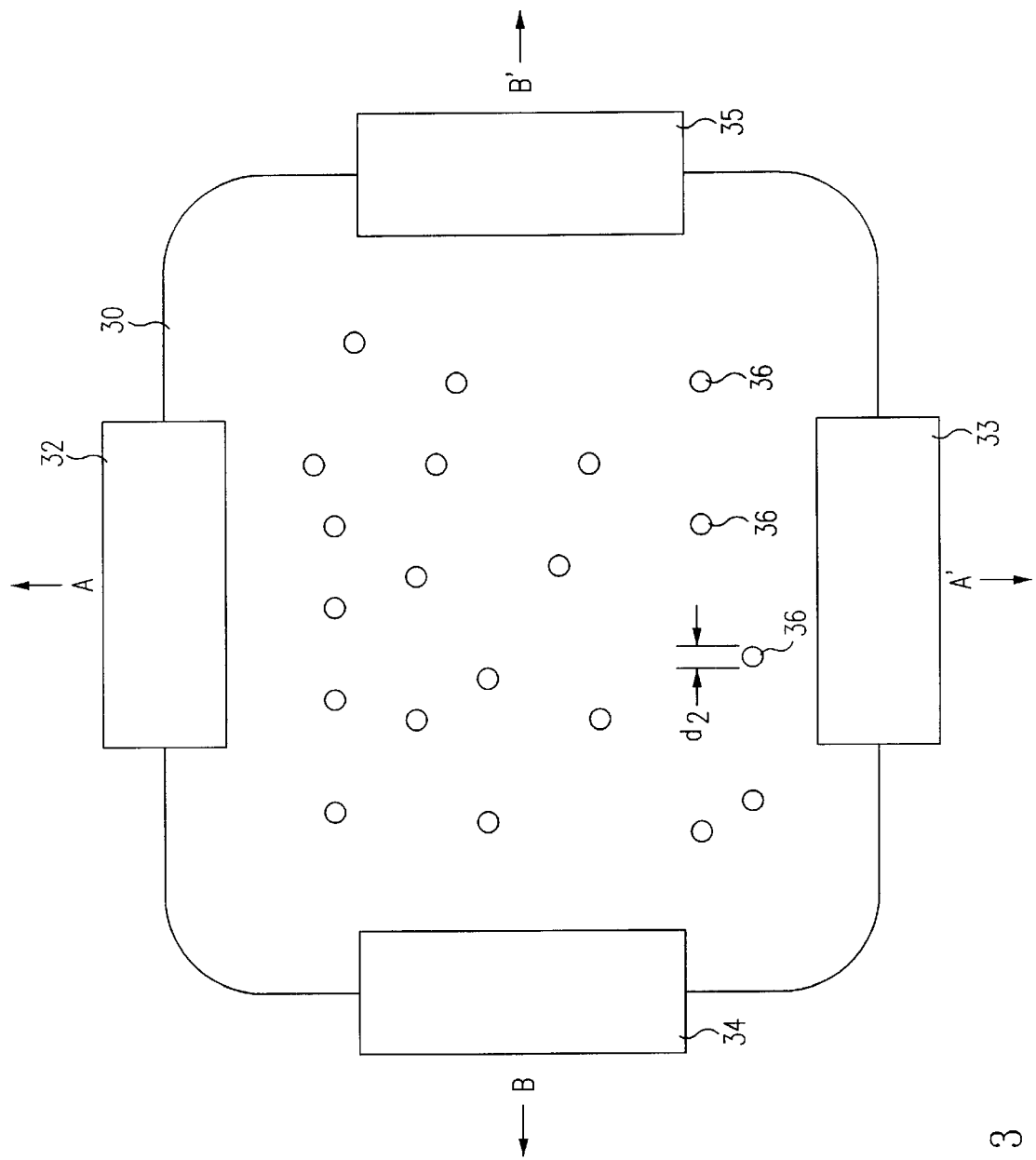
FIG. 3 shows a porous membrane in sheet form in a hyper-expanded state. Use of the same reference symbols in different figures indicates similar items.

In accordance with another embodiment of the present invention, FIG. 3 shows a sheet of an elastic material that is held in a symmetrical hyper-expanded state by clamps 32, 33, 34, and 35. Sheet 30 is stretched in the opposing directions A–A' and B–B'. While sheet 30 is in this hyper-expanded state, apertures 36 having a diameter $d_2$ are formed through sheet 30 using any of the known aperture-forming techniques, as described above. After apertures 36 are formed, sheet 30 is removed from clamps 32, 33, 34, and 35. Sheet 30 may then be formed into a cylindrical shape for use as a porous wall for balloon assemblies 10, 10-1, or 10-2, or some other balloon assembly.

Although the invention has been described with reference to particular embodiments, the description is only an example of the invention's application and should not be taken as a limitation. Various other adaptations and combinations of features of the embodiments disclosed are within the scope of the invention as defined by the following claims.

I claim:

1. A method for forming a porous membrane for a balloon catheter, the method comprising:
   forming an elastic material into an enclosed form having an interior region;
   expanding said closed form beyond an intended deployment expansion to a hyper-expanded state by infusing a fluid under pressure into said interior region;
   forming a plurality of apertures in said elastic material while in said hyper-expanded state; and
   maintaining said pressure in said interior region by continuing to infuse said fluid while said apertures are being formed.

2. The method of claim 1, wherein said hyper-expanded state is at least 25% greater than said intended deployment expansion.

3. The method of claim 1, wherein said hyper-expanded state is at least two times said intended deployment expansion.

4. The method of claim 1, wherein forming said plurality of apertures comprises an act selected from the group consisting of mechanical punching, mechanical drilling, directing a laser beam at said enclosed form, directing an ion beam at said enclosed form, and directing an electron beam at said enclosed form.

5. The method of claim 1, wherein said elastic material is a polymer.

6. The method of claim 5, wherein said elastic material is selected from the group consisting of polyurethane, latex, and silicone.

7. The method of claim 1, further comprising forming an outside wall of a balloon assembly for a balloon catheter with said elastic material.

8. A method for forming a porous balloon, comprising:
   forming a balloon of an elastic material, said balloon having an outer wall with an intended deployment diameter $D_1$;
   inflating said balloon to a diameter $D_2$ by infusing a fluid under pressure into said balloon, wherein $D_2$ is greater than $D_1$; and
   forming a plurality of apertures having a diameter $d_2$ in said outer wall while said outer wall is at said diameter $D_2$ by continuing to infuse said fluid under pressure so that said apertures have a smaller diameter $d_1$ while said outer wall is at said intended deployment diameter $D_1$.

9. The method of claim 8, wherein $D_2$ is at least 25% greater than $D_1$.

10. The method of claim 8, wherein $D_2$ is at least two times $D_1$.

11. The method of claim 8, wherein forming said plurality of apertures comprises an act selected from the group consisting of mechanical punching, mechanical drilling, directing a laser beam at said enclosed form, directing an ion beam at said enclosed form, and directing an electron beam at said enclosed form.

12. The method of claim 8, wherein said elastic material is a polymer.

13. The method of claim 8, wherein said elastic material is selected from the group consisting of polyurethane, latex, and silicone.

14. The method of claim 8, further comprising attaching said porous balloon to a balloon catheter.

15. A method of making a porous balloon for a catheter assembly for delivery of therapeutic agents to the anatomy of a patient, comprising:
   forming a cylinder having a closed end and an open end from an elastic material;
   applying a flow of fluid under pressure to said open end to expand said cylinder to a hyper-expanded state, wherein said hyper-expanded state is maintained by further application of said flow of fluid under pressure;
   forming apertures in said cylinder while said cylinder is in said hyper-expanded state, wherein said hyper-expanded state is maintained by application of said flow of fluid under pressure;
   removing said closed end from said cylinder to form said porous balloon.

16. The method of claim 15, further comprising mounting at least one said porous balloon on said catheter assembly.

* * * * *